(12) United States Patent
Edouard (10) Patent No.: US 11,730,428 B2
(45) Date of Patent: Aug. 22, 2023

(54) METHODS, APPARATUS AND COMPUTER PROGRAMS FOR DETERMINING FREQUENCIES OF BIOSIGNALS

(71) Applicant: WITHINGS, Issy les Moulineaux (FR)

(72) Inventor: Paul Edouard, Malakoff (FR)

(73) Assignee: WITHINGS, Issy les Moulineaux (FR)

( * ) Notice: Subject to any disclaimer, the term of this patent is extended or adjusted under 35 U.S.C. 154(b) by 224 days.

(21) Appl. No.: 16/128,169

(22) Filed: Sep. 11, 2018

(65) Prior Publication Data
US 2019/0076097 A1   Mar. 14, 2019

(30) Foreign Application Priority Data
Sep. 13, 2017   (EP) ..................... 17190945

(51) Int. Cl.
| | | |
|---|---|---|
| *A61B 5/00* | (2006.01) | |
| *A61B 5/024* | (2006.01) | |
| *A61B 5/11* | (2006.01) | |
| *A61B 5/0535* | (2021.01) | |
| *A61B 5/08* | (2006.01) | |
| *A61B 5/0245* | (2006.01) | |
| *A61B 5/316* | (2021.01) | |
| *A61B 5/0215* | (2006.01) | |

(52) U.S. Cl.
CPC .......... *A61B 5/7225* (2013.01); *A61B 5/0024* (2013.01); *A61B 5/0245* (2013.01); *A61B 5/02156* (2013.01); *A61B 5/02444* (2013.01); *A61B 5/0535* (2013.01); *A61B 5/0816* (2013.01); *A61B 5/1102* (2013.01); *A61B 5/316* (2021.01); *A61B 5/7246* (2013.01)

(58) Field of Classification Search
CPC . A61B 5/7225; A61B 5/0024; A61B 5/02444; A61B 5/0245; A61B 5/04014; A61B 5/0535; A61B 5/0816; A61B 5/1102; A61B 5/7246
USPC ......................................... 600/481
See application file for complete search history.

(56) References Cited

U.S. PATENT DOCUMENTS

| | | | |
|---|---|---|---|
| 2011/0295127 A1* | 12/2011 | Sandler | ......... A61B 7/026 600/484 |
| 2014/0364750 A1 | 12/2014 | Brumfield | |
| 2018/0000423 A1* | 1/2018 | Kanishima | ........... A61B 5/11 |

OTHER PUBLICATIONS

European Search Report Application No. EP 17190945.0 dated Mar. 1, 2018.

* cited by examiner

*Primary Examiner* — Alex M Valvis
*Assistant Examiner* — Chanel J Jhin
(74) *Attorney, Agent, or Firm* — Pillsbury Winthrop Shaw Pittman LLP (57) ABSTRACT

A method, apparatus and computer program wherein the method comprises: identifying a plurality of extrema points in a detected biosignal; comparing the identified extrema points with a plurality of sets of reference points wherein different sets of reference points correspond to different frequencies of the biosignal; and identifying the set of reference points that most closely fit the identified extrema points to determine a frequency of the biosignal.

23 Claims, 6 Drawing Sheets

Fig. 6 ly, examples of the disclosure there may be provided an apparatus comprising means for performing any of the methods described above.

METHODS, APPARATUS AND COMPUTER PROGRAMS FOR DETERMINING FREQUENCIES OF BIOSIGNALS

CROSS-REFERENCE TO RELATED APPLICATION

This application claims priority under the Paris Convention to European Patent Application No. 17190945.0 filed on Sep. 13, 2017.

FIELD OF THE DISCLOSURE

Examples of the present disclosure relate to methods, apparatus and computer programs for determining frequencies of biosignals.

BACKGROUND OF THE DISCLOSURE

The frequencies of biosignals generated by a user's body provide information about a user's health and wellbeing. For instance they may provide information about a user's heart rate or a respiration rate. It can be difficult to extract useful information from detected biosignals as the detected biosignals can have low amplitudes and can be very noisy. It is therefore useful to provide methods and apparatus which can reliably extract useful information from detected biosignals.

BRIEF SUMMARY OF THE DISCLOSURE

According to various, but not necessarily all, examples of the disclosure there may be provided a method comprising: Identifying a plurality of extrema points in a detected biosignal; comparing the identified extrema points with a plurality of sets of reference points wherein different sets of reference points correspond to different frequencies of the biosignal; and identifying the set of reference points that most closely fit the identified extrema points to determine a frequency of the biosignal.

The biosignal may comprise information indicative of at least one of; heart rate, respiration rate.

The biosignal may comprise at least one of: ballistocardiogram signal, impedance plethysmogram signal.

Identifying the set of reference points that most closely fit the identified extrema points may comprise assigning a value to points within the sets of reference points where the value provides an indication of an off-set between the reference points and the identified extrema points. Identifying the set of reference points that most closely fit the identified extrema points may comprise identifying the set of reference points with the highest assigned values. Identifying the set of reference points may comprise using a matching window. The method may comprise determining the distance between an identified extrema point and a reference point along one or more axis of the matching window to determine how closely a reference point fits an identified extrema point.

The sets of reference points are obtained from the detected biosignal. The reference points are obtained by applying an offset to the identified extrema points to represent different frequencies.

The method may comprise filtering the detected biosignal.

According to various, but not necessarily all, examples of the disclosure there may be provided an apparatus comprising: means for identifying a plurality of extrema points in a detected biosignal; means for comparing the identified extrema points with a plurality of sets of reference points wherein different sets of reference points correspond to different frequencies of the biosignal; and means for identifying the set of reference points that most closely fit the identified extrema points to determine a frequency of the biosignal.

According to various, but not necessarily all, examples of the disclosure there may be provided an apparatus comprising means for performing any of the methods described above.

According to various, but not necessarily all, examples of the disclosure there may be provided an apparatus comprising: circuitry arranged to identify a plurality of extrema points in a detected biosignal; circuitry arranged to compare the identified extrema points with a plurality of sets of reference points wherein different sets of reference points correspond to different frequencies of the biosignal; and circuitry arranged to identify the set of reference points that most closely fit the identified extrema points to determine a frequency of the biosignal.

According to various, but not necessarily all, examples of the disclosure there may be provided an apparatus comprising circuitry arranged to perform any of the methods described above.

According to various, but not necessarily all, examples of the disclosure there may be provided a system comprising an apparatus as described above and one or more electrodes arranged to detect the biosignal.

The one or more electrodes may be located remotely to the apparatus and may be arranged to transmit information indicative of the detected biosignals to the apparatus via a wireless communication link.

According to various, but not necessarily all, examples of the disclosure there may be provided a computer program comprising computer program instructions that, when executed by processing circuitry, enable: identifying a plurality of extrema points in a detected biosignal; comparing the identified extrema points with a plurality of sets of reference points wherein different sets of reference points correspond to different frequencies of the biosignal; and identifying the set of reference points that most closely fit the identified extrema points to determine a frequency of the biosignal.

According to various, but not necessarily all, examples of the disclosure there may be provided a computer program comprising program instructions for causing a computer to perform any of the methods described above.

According to various, but not necessarily all, examples of the disclosure there is provided examples as claimed in the appended claims.

BRIEF DESCRIPTION OF THE DRAWINGS

For a better understanding of various examples that are useful for understanding the detailed description, reference will now be made by way of example only to the accompanying drawings in which.

DETAILED DESCRIPTION OF THE DISCLOSURE

The Figures show methods, apparatus and computer programs for determining frequencies of biosignals. The methods, apparatus and computer programs work by comparing identified extrema points with sets of reference points. This provides a method which has low computational requirements which may provide for an efficient apparatus. Also the method does not require any calibration signals to be obtained. This may enable the frequencies of the biosignals to be determined more quickly.

Figure 1:
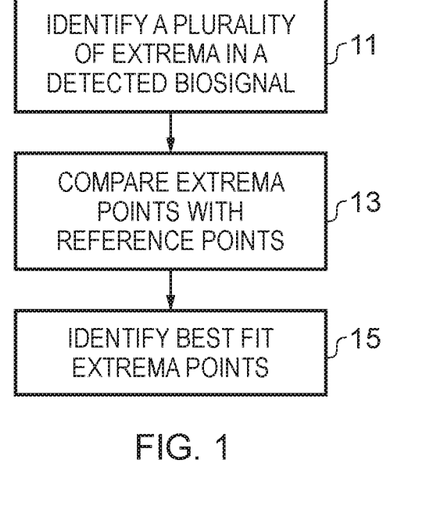
FIG. 1 illustrates a method.

FIG. 1 illustrates a method of determining frequencies of bio signals according to examples of the disclosure.

The method comprises, at block 11, identifying a plurality of extreme points in a detected biosignal. The biosignal may be any detectable signal which is generated by the user's body. The biosignal could be a bioelectric signal, a biomechanical signal or any other suitable type of signal. The biosignal may comprise an autonomic signal. The autonomic signal may be controlled subconsciously by the user. The biosignals may comprise electrical or mechanical signals that are generated within the user's body by the user's heartbeat and/or breathing so that the biosignal comprises information indicative of a user's heart rate and/or respiration rate. In some examples of the disclosure the biosignal could comprise a ballistocardiogram signal, impedance plethysmogram signal or any other suitable type of signal.

The biosignal could be detected using any suitable means. In some examples the biosignal could be detected by one or more sensing electrodes which may be coupled to the body of the user. In other examples the biosignals could be detected by one or more sensors that are positioned underneath a user. For example a sensor positioned underneath a user could detect biomechanical signals of a user lying or standing over the sensors. This may enable the biosignals of the user to be monitored while the user is sleeping or resting.

The extrema points that are identified may be any maxima and minima points in the detected signal. Any suitable technique may be used to identify the extrema points.

At block 13 the method comprises comparing the identified extrema points with a plurality of sets of reference points. The different sets of reference points correspond to different frequencies of the biosignal.

Each set of reference points may comprise a data set which indicates the expected positions of extrema for a biosignal having a particular frequency. The different sets of reference points may be stored in memory circuitry once the biosignal is detected. The sets of reference points are based on the identified extrema points and may be determined once the input biosignal has been sampled. The different sets of reference points may be obtained by applying an offset to the identified extrema points to represent different frequencies or by any other suitable method.

As the sets of reference points are obtained and stored in the memory circuitry 27 as the input biosignal is sampled this may be considered as a type of "on-stream" calibration which means that there is no need for any calibration signals to be obtained or for any other reference biosignals to be detected.

The sets of reference points that are available may correspond to the expected frequencies of the parameter that is being measured. For example where the method is being used to determine a user's heart rate the sets of reference points that are used may cover the range of expected heart rates. The range of expected heart rates might be, for example between 35 to 110 beats per minute. This could be used to detect the heart rate of a user at rest. In some examples the sets of reference points may cover the whole of this range to ensure that the same methods and apparatus could be used for any patient. In other examples the sets of reference points could cover a subset of this range. This could be used it if is known beforehand what the expected range for the heart beat would be, For instance a fit adult would have a lower heart rate than a young child.

Any suitable technique may be used to compare the identified extrema points with the reference points. In some examples the comparison may comprise assigning a value to each point within a set of reference points where the value provides an indication of an off-set between the reference points and the identified extrema points. The values could be assigned so that the highest value is assigned to the reference points with the smallest offset. This process could then be repeated for each of the sets of the reference points.

At block 15 the method comprises identifying the set of reference points that most closely fit the identified extrema points to determine a frequency of the biosignal.

Any suitable technique may be used to identify the set of reference points that most closely fit the identified extrema points. In some embodiments the total assigned values for each of the sets of the reference points could be determined. The best fit set of reference points would be the set of reference points with an optimised value. In some examples the optimised value could be the highest overall value. In other examples the optimised value could be a mean value or any other suitable value. The frequency of the biosignal therefore corresponds to the frequency of the identified set of reference points.

The above described method therefore provides an efficient method for determining the frequency of a biosignal. It is to be appreciated that in implementations of the disclosure the method may comprise other blocks that are not shown in FIG. 1. For instance, in some examples the detected biosignal may be filtered before the extrema points are identified.

Figure 2:
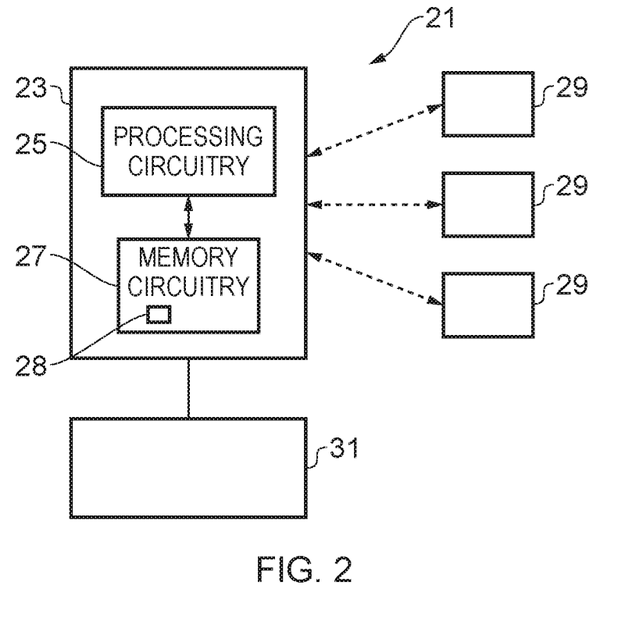
FIG. 2 illustrates a system comprising an example apparatus.

FIG. 2 schematically illustrates a system 21 which could be used to implement example methods as described above. The system 21 comprises a plurality of sensors 29, an apparatus 23 and a user output device 31.

In some examples of the disclosure the components of the system 21, the sensors 29, the apparatus 23 and the user output device 31 may be located remotely from each other. In such examples communication links may be provided between the respective components. The communication links could be wired or wireless communication links. For instance, in some examples the sensors 29 could be provided in sensing pads that could be positioned adjacent to, or in contact with, a user. The sensing pads may detect the biosignals and transmit the biosignals to an apparatus 23 to enable the method described above to be performed on the detected biosignals. Once the frequency of the detected biosignal has been determined the apparatus 23 may transmit information indicative of the determined frequency to the output device 31.

In other examples the sensors 29, apparatus 23 and output device 31 may be provided in a single device. For example a wearable electronic device may comprise sensors 29 an apparatus 23 comprising processing circuitry 25 and also an output device 31.

The plurality of sensors 29 may comprise any means which enables a biosignal to be detected from a user and enables an output to be provided indicative of the detected biosignal. The types of sensors 29 that are used may depend on the type of biosignal that is to be detected and the parameter of the user that is to be monitored. For instance, where the biosignal comprises a ballistocardiogram signal the sensors 29 comprise force sensors. The force sensors could comprise piezoelectric material, Wheatstone bridges or any other suitable types of sensors 29.

Figure 6:
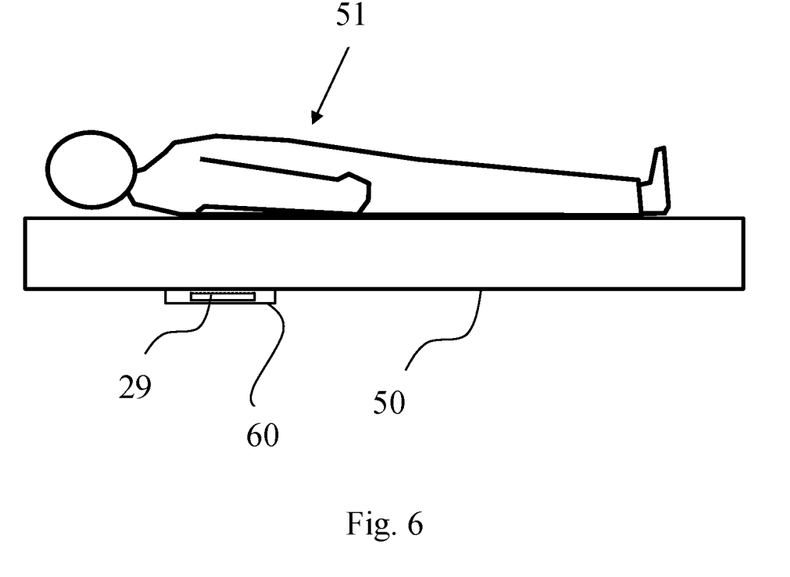

The sensors 29 may be positioned in any suitable location relative to the user. In some examples the sensors 29 may be positioned underneath the user. For instance where the biosignal comprises a ballistocardiogram signal the plurality of sensors 29 could be positioned underneath the user's torso as the user is lying down. The sensors 29 could be provided underneath a mattress 50 while the user 51 is lying on the mattress 50, as shown in FIG. 6. In FIG. 6, the sensors 29 are provided in a sensing pad 60. In other examples the sensors 29 may be positioned in other locations. In some examples different sensors 20 of the plurality of sensors 29 may be positioned in different locations relative to the user's body so that the biosignals can be detected from different parts of the user.

In the example system 21 of FIG. 2 a plurality of sensors 29 are provided. It is to be appreciated that in other examples of the disclosure a single sensor 29 could be used.

In the example system 21 of FIG. 2 the plurality of sensors 29 are coupled to the apparatus 23 via a communication link. The communication link could be a wired or wireless communication link. In such examples the communication link may comprise a wireless communication link such as Bluetooth, Bluetooth Low Energy, Bluetooth Smart, 6LoW-Pan (IP$_v$6 over low power personal area networks) ZigBee, ANT+, near field communication (NFC), Radio frequency identification (RFID), wireless local area network (wireless LAN) or any other suitable communication link.

The apparatus 23 comprises means which may be arranged to obtain the output signals from the sensors 29 and use these signals to determine the frequency of the biosignals. In the example of FIG. 2 the apparatus 23 comprises processing circuitry 25 and memory circuitry 27. It is to be appreciated that the apparatus 23 may also comprise other components which have not been illustrated in FIG. 2. For instance the apparatus 23 may comprise one or more transceivers which may be arranged to receive the signals from the sensors 29 and transmit a signal indicative of the determined frequency to the output device 31.

The processing circuitry 25 and memory circuitry 27 are described in further detail with reference to FIG. 3. The processing circuitry 25 and the memory circuitry 27 may be arranged to perform the example methods as described above. In such example the sets of reference points 28 may be stored within the memory circuitry 27.

In the example system 21 of FIG. 2 the apparatus 23 is coupled to an output device 31. The apparatus 23 could be coupled to the output device 31 via any suitable means. For instance a wired or wireless communication link could be provided. The wireless communication link could be a low power communication link as described above. Where a wireless communication link is provided this may enable the apparatus 23 to be moved relative to the output device 31. In other examples the apparatus 23 could be provide within the same device as the output device 31. For instance, a wearable electronic device could be provided.

The output device 31 may comprise any means which may be arranged to provide an output to a user where the output is indicative of the frequency of the detected biosignal.

In some examples the output device 31 may comprise a display. The display may comprise any means which may enable visual information to be provided to a user. The visual information could comprise information such as a graph and/or number indicative of the frequency of the detected biosignal or of any other suitable information.

In some examples the output device 31 may comprise an audio output device. The audio output device may comprise any means, such as a loudspeaker, which may enable an audio signal to be provided to the user.

In some examples the output device 31 may comprise a haptic output device which may be arranged to provide haptic feedback to a user. For instance the output device could comprise a vibrator or other means for providing a tactile alert to the user.

In the example system 21 of FIG. 2 a single output device 31 is provided. In other examples the system could comprise a plurality of output devices 31. For instance, a first output device 31 may be arranged to provide an output to a user and a second output device 31 may be arranged to provide an output to a medical professional.

In some examples the system 21 may be arranged so that the output device 31 provides an output whenever the frequency of a biosignal is detected. This may enable a user to obtain constant information about the biosignals. In some examples the system 21 may be arranged so that the output device 31 provides an output when the frequency of the biosignal exceeds a threshold. For example, an alarm may be triggered if the user's heart rate drops below a certain frequency or if the user's hear rate rises above a given frequency.

Figure 3:
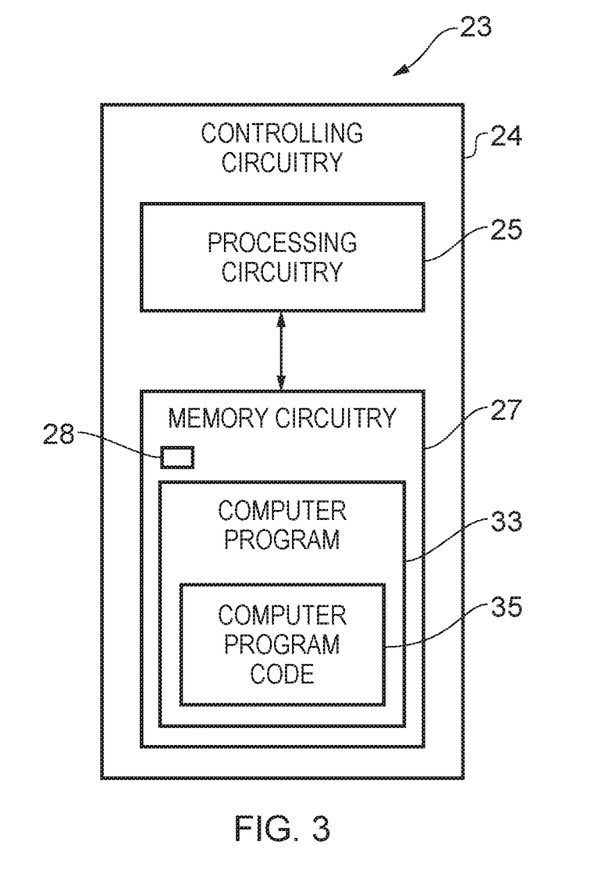
FIG. 3 illustrates an example apparatus.

FIG. 3 schematically illustrates an apparatus 23 according to examples of the disclosure. The apparatus 23 illustrated in FIG. 1 may be a chip or a chip-set. The apparatus could be provided within any suitable device. The apparatus 23 could be provided within a dedicated sensing device or within any suitable computing device.

The apparatus 1 comprises a controlling circuitry 24. The controlling circuitry 24 may also provide means for performing the methods or at least part of the methods of examples of the disclosure.

The apparatus 23 comprises a processing circuitry 25 and a memory circuitry 27. The processing circuitry 25 may be configured to read from and write to the memory circuitry 27. The processing circuitry 25 may comprise one or more processors. The processing circuitry 25 may also comprise an output interface via which data and/or commands are output by the processing circuitry 25 and an input interface via which data and/or commands are input to the processing circuitry 25.

The memory circuitry 27 may be configured to store sets of reference points 28. The sets of reference points 28 may be stored in the memory circuitry 27 so that they can be retrieved by the processing circuitry 25 when the methods described above are being implemented.

The memory circuitry 27 may be configured to store one or more computer programs 33 comprising computer program instructions (computer program code 35) that controls the operation of the apparatus 23 when loaded into processing circuitry 25. The computer program instructions, of the computer program 33, provide the logic and routines that enable the apparatus 23 to perform the example methods illustrated in FIG. 1. The processing circuitry 25 by reading the memory circuitry 27 is able to load and execute the computer program 33.

The computer program 33 may arrive at the apparatus 23 via any suitable delivery mechanism. The delivery mechanism may be, for example, a non-transitory computer-readable storage medium, a computer program product, a memory device, a record medium such as a compact disc read-only memory (CD-ROM) or digital versatile disc (DVD), or an article of manufacture that tangibly embodies the computer program. The delivery mechanism may be a signal configured to reliably transfer the computer program 33. The apparatus may propagate or transmit the computer program 33 as a computer data signal. In some examples the computer program code 35 may be transmitted to the apparatus 23 using a wireless protocol such as Bluetooth, Bluetooth Low Energy, Bluetooth Smart, 6LoWPan (IP$_v$6 over low power personal area networks) ZigBee, ANT+, near field communication (NFC), Radio frequency identification (RFID), wireless local area network (wireless LAN) or any other suitable protocol.

Although the memory circuitry 27 is illustrated as a single component in the figures it is to be appreciated that it may be implemented as one or more separate components some or all of which may be integrated/removable and/or may provide permanent/semi-permanent/dynamic/cached storage.

Although the processing circuitry 25 is illustrated as a single component in the figures it is to be appreciated that it may be implemented as one or more separate components some or all of which may be integrated/removable.

References to "computer-readable storage medium", "computer program product", "tangibly embodied computer program" etc. or a "controller", "computer", "processor" etc. should be understood to encompass not only computers having different architectures such as single/multi-processor architectures, Reduced Instruction Set Computing (RISC) and sequential (Von Neumann)/parallel architectures but also specialized circuits such as field-programmable gate arrays (FPGA), application-specific integrated circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term "circuitry" refers to all of the following:

(a) hardware-only circuit implementations (such as implementations in only analog and/or digital circuitry) and (b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions) and the circuits, such as a microprocessor(s) or a portion of a microprocessor(s), that require software or firmware for operation, even if the software or firmware is not physically present.

This definition of "circuitry" applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in a server, a cellular network device, or other network device.

Figure 4A:
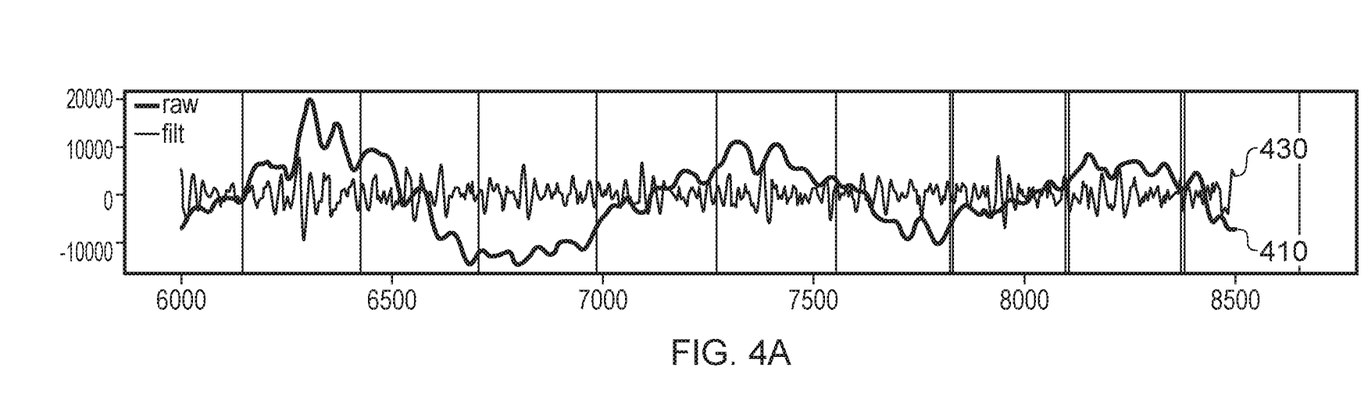
FIGS. 4A to 4C illustrate example results.
Figure 4B:
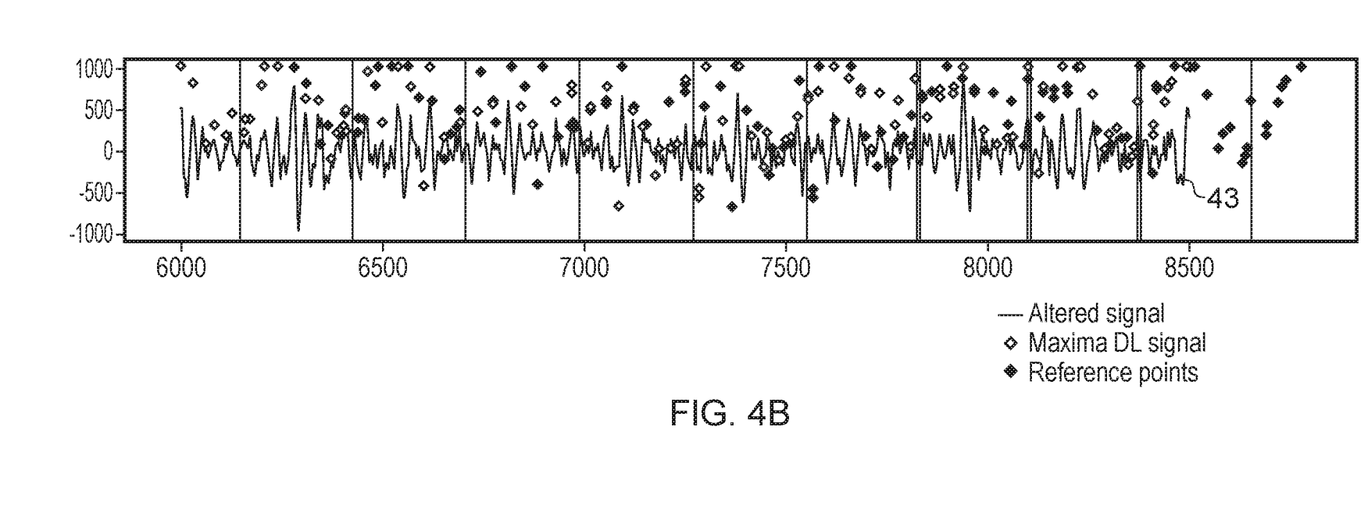
Figure 4C:
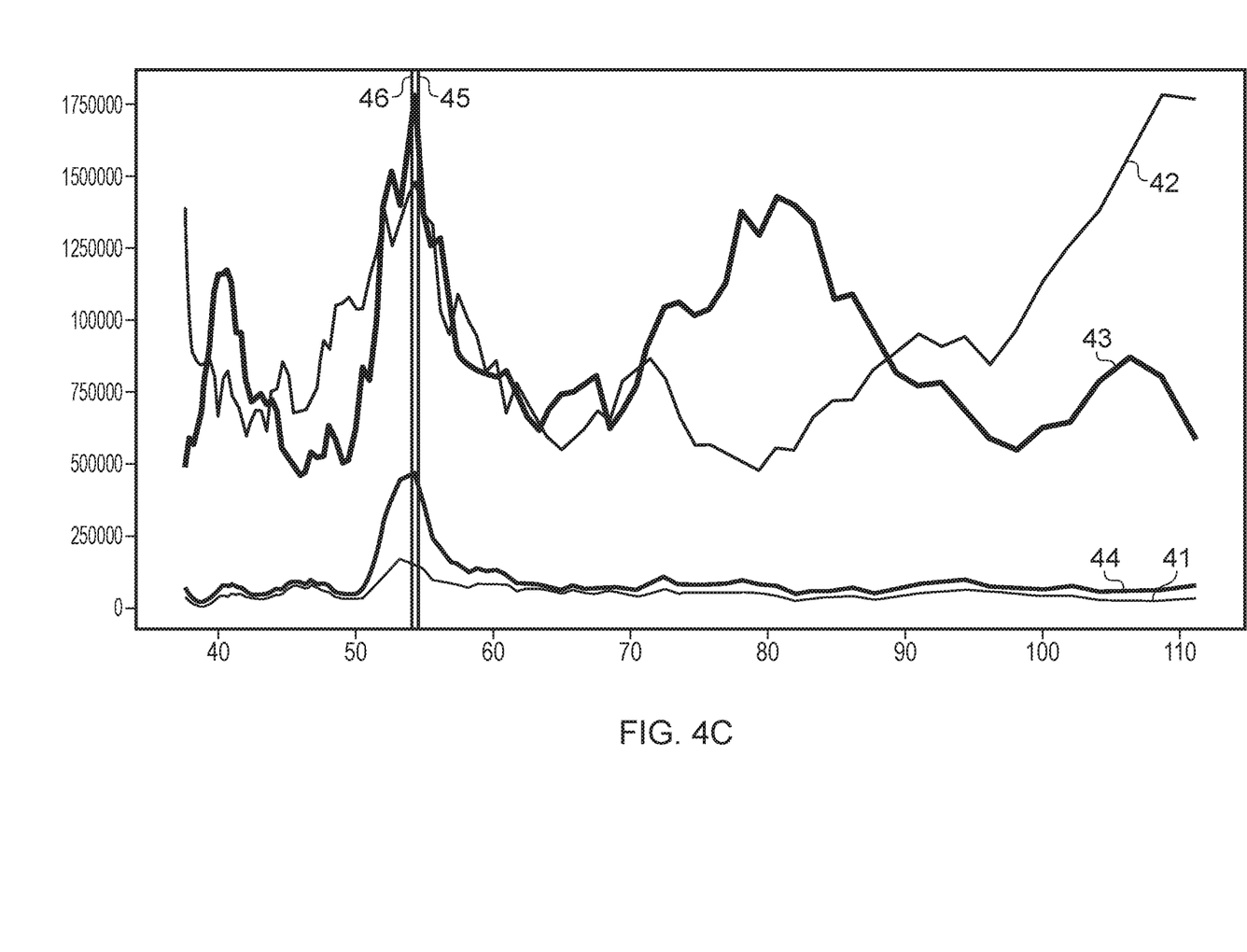

FIGS. 4A to 4C illustrate example results which may be obtained using examples of the disclosure. In the example of FIG. 4A to 4C the frequency of a user's heart rate is calculated. It is to be appreciated that in other examples the method could be used to determine the frequency of other biometric parameters such as respiration rate.

Plot 410 in FIG. 4A shows the raw unfiltered biosignal which is obtained by the sensors 29. The unfiltered biosignal is filtered to obtain plot 430. In the examples of FIGS. 4A to 4C a band pass filter may be used to remove low frequency components and to reduce the noise in the signal. The low frequency components may be a result of the user's breathing. The noise that is removed by the band pass filter could be high frequency noise.

A sample of the signal is obtained. The sample lasts for any suitable duration of time. The duration of the sample signal must last for long enough to ensure that enough extrema points are obtained and stored to enable reliable matching between the biosignal and the reference points. In the examples of FIGS. 4A to 4C the sample has a length of ten seconds. Other time durations could be used in other examples of the disclosure. For instance the time duration could be of the order of several seconds.

In some examples only the obtained extrema points need to be stored. The remainder of the signal can be discarded. This may provide for a more efficient use of memory circuitry 27 and processing circuitry 25.

In FIG. 4B the extrema of the signal have been identified. In the example of FIG. 4B only the identified maxima are shown. It is to be appreciated that the minima could also be identified instead of or in addition to the maxima. The identified minima are not shown in FIG. 4B for clarity.

The identified extrema may be normalized.

The extrema are then compared with a plurality of different sets of reference points. Each set of reference points is obtained by shifting the identified extrema points by a respective offset in time. A set of reference points is shown in FIG. 4B. Only one set of reference points is shown for clarity. The set of reference points shown in FIG. 4B represents a frequency of 60 beats per minute. It is to be appreciated that other sets of reference points representing different frequencies would also be used in implementations of the method. The above mentioned time duration of the signal sample should ideally be at least double the period of the frequency of represented by the reference points. In the above example where the reference points represent a signal of 60 beats per minute, then the signal sample duration should be at least two seconds.

In examples of the disclosure each reference point within the set is compared with the closest extrema from the biosignal. Each reference point within the set is assigned a score where the score is indicative of how close the reference point is to the identified extreme. In some examples the assigned score may be higher if there is a close fit between the reference points and the extrema. This gives reference points with a good correlation to the extrema a higher score than reference points with a poor correlation.

Any suitable methods may be used to determine whether or not there is a close fit between the reference points and the extrema. In some examples the method may comprise mapping a matching window onto the extreme points where the matching window has an x axis and y axis. The x axis and the y axis are perpendicular to each other. The distance between the extrema and the reference points on each of the axis can be determined to determine how closely the reference points fit the extrema.

The total score for a set of reference points can then be determined by summing the scores assigned to each of the reference points within a set. FIG. 4C shows a plot of the scores for each of the sets of reference points.

In FIG. 4C the x axis represents the frequency of the reference points in beats per minute and the y axis represents the scores assigned to these sets of reference points. The frequency of the reference points ranges from 35 to 110 beats per minutes.

In FIG. 4C plot 41 represents the score of the first harmonic, plot 42 represents the score of the second harmonic and plot 43 represents the score of the third harmonic. Plot 44 represents the final score which is obtained by multiplying the scores assigned to the different harmonics. Vertical line 45 shows a predicted score and vertical line 46 shows a reference score. This shows a peak score around 55 beats per minute which is therefore indicative of the user's heart rate.

Figure 5:
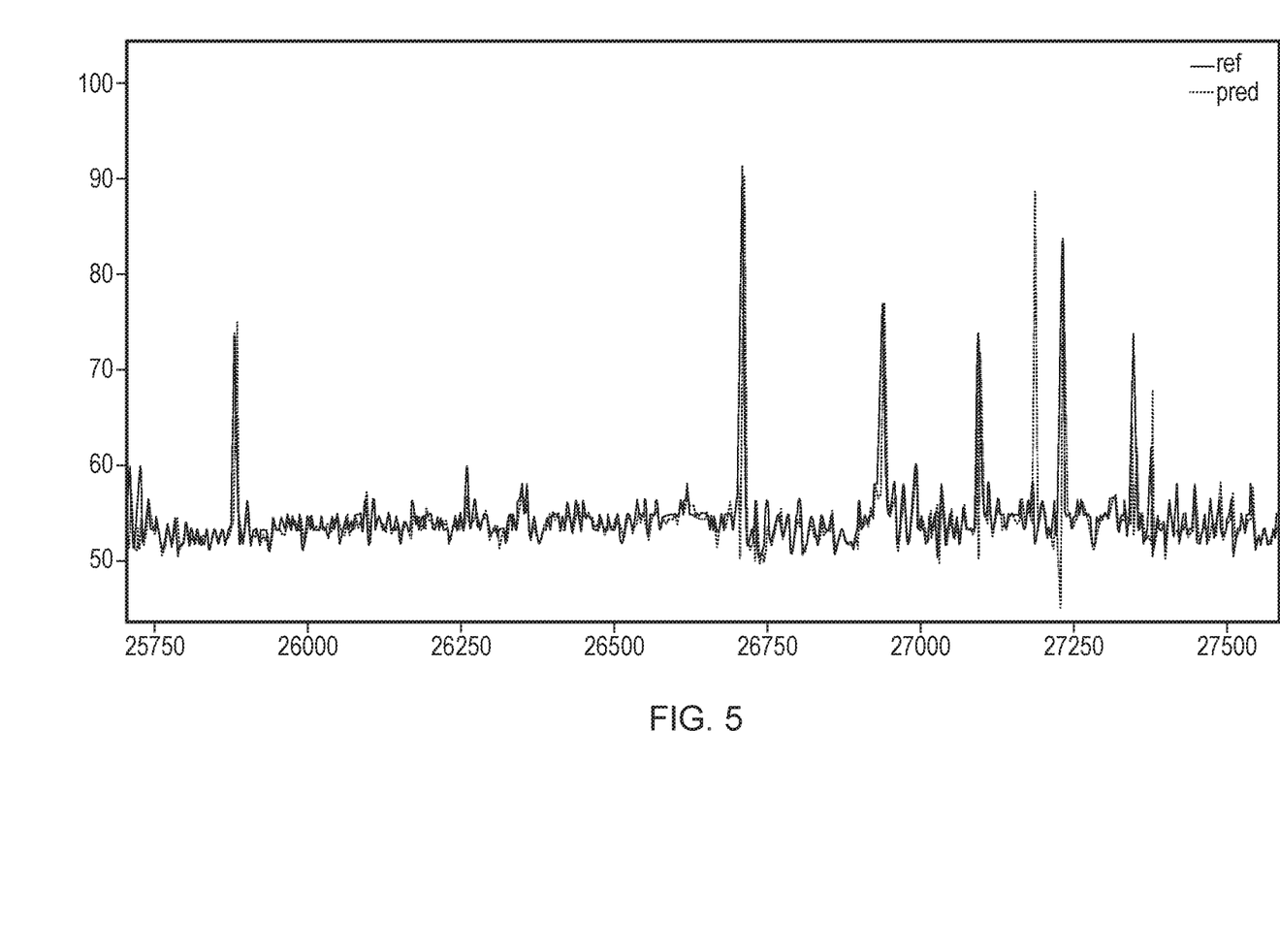
FIG. 5 illustrates a comparison between results obtained using examples of the disclosure and ECG data, and
FIG. 6 schematically illustrates a sensing pad that includes sensors positioned under a mattress.

FIG. 5 illustrates a comparison between examples of the disclosure and ECG data.

In FIG. 5, the x axis represents time, sampled at 10 Hz, and the y axis represents heart rate, in beats per minutes. The total duration of the recording shown is 4 minutes.

"ref" is the beat-to-beat heart rate obtained by an ECG, and "pred" is the beat-to-beat heart rate obtained by the disclosure.

The pikes are short heart rate accelerations that can naturally occur during the night, and a small oscillation can be observed around the heart rate baseline, caused by the modulation of heart rate by respiration cycles.

Both the pikes and the small oscillations are identically detected by the ECG and the disclosure.

This shows that the methods and apparatus 23 used in examples of the disclosure can produce results with an accuracy comparable to ECG data."

Examples of the disclosure provide the advantage that the frequency of a bio signal can be determined from the extreme of the signal. The rest of the signal does not need to be used. This reduces the amount of data that needs to be processed and stored, and so significantly reduces the computational requirements. This provides for an efficient apparatus 23. For instance, it may provide for an efficient use of the memory circuitry 27. In some examples only around 2 kb of RAM might be needed to implement the describe methods. It may also provide for an efficient use of the processing circuitry 25, for instance it may take around 0.5 ms to use the described methods to calculate the frequency of a heart rate, or other biosignal, using 1.6 GHz processing circuitry 25. It may take around 200 ms to use the described methods to calculate the frequency of a heart rate, or other biosignal, using 120 MHz processing circuitry 25, such as a Kinetis® "K_22" 120 MHz processor.

This also provides the advantage that the frequency is determined by comparing the detected biosignal with sets of reference points. The sets of reference points are based on the identified extrema points and may be determined once the input biosignal has been sampled. This provides for "on-stream" calibration which occurs as the input biosignal is being detected. This means that as soon as the biosignal is detected and sampled it can be compared to the obtained reference points. There is no need to obtain separate calibration signals or to compare different detected bio signals. This may enable the frequency of the detected biosignal to be determined quickly. If the biosignal is being monitored for an extended period of time it is useful to be able to quickly determine the frequency of the biosignal as this may enable feedback to be provided to a user as soon as there is a change in the frequency of the biosignal.

The system 21 also provides the benefit that the precise location of the one or more sensors 29 does not matter. The methods can be implemented so long as the sensors 29 are providing a periodic signal. This means that the heart rates can be measured even if a user moves relative to the sensors. This could be useful where the sensors 29 are positioned underneath a mattress as the frequency of the biosignals can still be determined even if the user moves on the mattress.

The method also enables the frequencies of the biosignals to be determined even where the detected signals have poor quality, for example, where the detected signals have a lot of noise. As the information of the extrema is used this enables the frequency to be determined even is there are no visible periodic patterns within the signal. Furthermore the use of the reference points also acts to remove outliers that represent extrema that are not indicative of the user's heartbeat.

In this description and claims the term coupled means operationally coupled. It is to be appreciated that any number of components may be provided between coupled elements including zero components.

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

The following algorithm may be used to implement examples of the disclosure:

```c
#define _POSIX_C_SOURCE 200809L
#include <stdlib.h>
#include <stdio.h>
#include <string.h>
#include <inttypes.h>
#include "utils/math_utils.h"
#include "utils/extrema.h"
#include "hr/hr_algo.h"
/* Extrema detector */
#define HR_DELTA_SAMPLES_EXTREMA (+AURA_FS/10)       // 25 samples minimum between two extrema
#define HR_APPLY_NORMALIZATION 1
#define HR_NORMALIZATION_WIN ((int32_t) (0.6*AURA_FS))
#define HR_EXTREMA_MEM (HR_NORMALIZATION_WIN / HR_DELTA_SAMPLES_EXTREMA)
#define HR_EXTREMA_WIN HR_SAMPLES_WINDOW             // 8 seconds
#define HR_EXTREMA_NORM_MEM (HR_EXTREMA_WIN / HR_DELTA_SAMPLES_EXTREMA)
/* Distance function */
#define MATCHING_WIN_X 12      // Half width of matching window
#define MATCHING_WIN_Y 300     // Half height of matching window
#define MATCHING_MIN_Y 200     // Minimum Y for considering the point
/* Peak tracking */
#define HR_PEAK_TRACKING_MEM (+30)
/* Macros */
#define MAX(X, Y) ( (X) > (Y) )? (X) : (Y)
#define MIN(X, Y) ( (X) > (Y) )? (Y) : (X)
#define ABS(X) ( ( (X) < 0 ) ? -(X) : (X) )
static const int32_t gauss[HR_GAUSS_LENGTH / 2] = {
    // Generated on http://t-filter.engineerjs.com/
    0, 0, 0, 0, 0, 0, 115, 192, 257, 251, 161, 24, -95, -145, -125, -89, -103, -191,
    -306, -362, -303, -169, -83, -178, -476, -834, -990, -709, 46, 1056, 1920, 2259
};
/************** PRIVATE FUNCTIONS ********************************/
static int16_t gaussian_filter_update(hr_algo_ctx_t * ctx, uint16_t adc_steps);
static int32_t matching_score(aura_xy_t * p1 , aura_xy_t * p2, int32_t win_x);
static int32_t self_match(aura_circbuf_t * ctx, int32_t offset, int32_t win_x);
static int32_t hr_algo_predict(hr_algo_ctx_t * ctx);
/************** PUBLIC FUNCTIONS ********************************/
/*****
 * Hard-coded behaviour is hard-coded
 */
static int32_t hr_tracking_transition(int32_t x_prev, int32_t x)
{
    int32_t dist = ABS(x_prev - x);
    if (dist < 30) {
        return (30 - dist);
    }
    return 1;
}
int32_t hr_algo_init(hr_algo_ctx_t * ctx)
{
    if (ctx == NULL) {
        return -1;
    }
    memset(ctx, 0, sizeof(hr_algo_ctx_t));
    aura_extrema_params_t params = {
        .delta_min=HR_DELTA_SAMPLES_EXTREMA,
        .apply_normalization=HR_APPLY_NORMALIZATION,
        .normalization_win=HR_NORMALIZATION_WIN,
        .extrema_mem=HR_EXTREMA_MEM,
        .extrema_win=HR_EXTREMA_WIN,
        .extrema_norm_mem=HR_EXTREMA_NORM_MEM
    };
    aura_extrema_init(&(ctx->extrema), &params);
    aura_peak_tracking_init(&(ctx->track), HR_PEAK_TRACKING_MEM,
            &hr_tracking_transition);
    return 0;
}
int32_t hr_algo_release(hr_algo_ctx_t * ctx)
{
    aura_extrema_release(&(ctx->extrema));
    aura_peak_tracking_release(&(ctx->track));
    return 0;
}
int32_t hr_algo_update(hr_algo_ctx_t * ctx, uint16_t adc_steps)
{
    int32_t tmp;
    tmp = adc_steps;
#if (defined TESTING_BUILD && defined LOG_HR_FILTER)
printf("~RAW,%d,%d\n", ctx->idx, tmp);
```

```
#endif
    tmp = gaussian_filter_update(ctx, adc_steps);
#if (defined TESTING_BUILD && defined LOG_HR_FILTER)
    printf("~FILT,%d,%d\n", ctx->idx, tmp);
#endif
    aura_extrema_update(&(ctx->extrema), tmp, 1);
    ctx->idx++;
    // Update the predicted HR once every 2 seconds
    if (ctx->idx % HR_SAMPLES_STEP == 0) {
        hr_algo_predict(ctx);
        return HR_RET_NEW_VAL;
    }
    return HR_RET_NO_NEW_VAL;
}
/************** PRIVATE FUNCTIONS ******************************/
static int32_t hr_algo_predict(hr_algo_ctx_t * ctx)
{
    int32_t i, offset, a, b, c;
    int32_t max_score = 0;
    ctx->hr = 0;
    for (i = 0; i < HR_N_SAMPLES; i++) {
        offset = HR_DOWNSAMPLE * (i + HR_SMIN);
        a = (self_match(&ctx->extrema.maxima_norm, offset, MATCHING_WIN_X) >> 6)
            * (self_match(&ctx->extrema.minima_norm, offset, MATCHING_WIN_X) >> 6);
        b = (self_match(&ctx->extrema.maxima_norm, offset*2, 2*MATCHING_WIN_X) >> 6)
            * (self_match(&ctx->extrema.minima_norm, offset*2, 2*MATCHING_WIN_X) >> 6);
        c = (self_match(&ctx->extrema.maxima_norm, offset*3, 2*MATCHING_WIN_X) >> 6)
            * (self_match(&ctx->extrema.minima_norm, offset*3, 2*MATCHING_WIN_X) >> 6);
        ctx->scores[i] = (a >> 12) * ((b + c) >> 12);
#if (defined TESTING_BUILD && (defined LOG_HR_FILTER || defined LOG_HR_DEBUG))
        int32_t bpm; //x100
        bpm = (100 * (60 * AURA_FS)) / offset;
        printf("&score,%d,%d,%d\n", ctx->idx, bpm, ctx->scores[i]);
        printf("&score1,%d,%d,%d\n", ctx->idx, bpm, a);
        printf("&score2,%d,%d,%d\n", ctx->idx, bpm, b);
        printf("&score3,%d,%d,%d\n", ctx->idx, bpm, c);
#endif
        if (ctx->scores[i] > max_score) {
            max_score = ctx->scores[i];
            ctx->hr = offset;
        }
    }
    aura_peak_tracking_update(&(ctx->track), ctx->scores, HR_N_SAMPLES, &(ctx->hr_tracked));
    ctx->hr_tracked = HR_DOWNSAMPLE*(ctx->hr_tracked + HR_SMIN);
    // Improvised exp filter
    ctx->hr_lowpassed = (ctx->hr_lowpassed*512 + ctx->hr_tracked*(1024 - 512)) / 1024;
    // Clip the HR just to be sure
    if (ctx->hr_lowpassed < HR_DOWNSAMPLE*HR_SMIN)
        ctx->hr_lowpassed = HR_DOWNSAMPLE*HR_SMIN;
    else if (ctx->hr_lowpassed > HR_DOWNSAMPLE*HR_SMAX)
        ctx->hr_lowpassed = HR_DOWNSAMPLE*HR_SMAX;
    return (10 * 60 * AURA_FS) / ctx->hr_lowpassed;
}
static int16_t gaussian_filter_update(hr_algo_ctx_t * ctx, uint16_t adc_steps)
{
    int16_t filtered;
    ctx->raw_buf[ctx->raw_buf_idx] = adc_steps;
    ctx->raw_buf[ctx->raw_buf_idx] -= 1 << 15; // unsigned -> signed
    filtered = convolve_short(ctx->raw_buf, HR_GAUSS_LENGTH, gauss, HR_GAUSS_LENGTH, ctx->raw_buf_idx);
    ctx->raw_buf_idx = (ctx->raw_buf_idx == HR_GAUSS_LENGTH-1) ? 0 : ctx->raw_buf_idx + 1;
    return filtered;
}
// this function must not be called with points such as term_x < 0
static inline int32_t matching_score(aura_xy_t * p1, aura_xy_t * p2, int32_t win_x)
{
    int32_t term_x, term_y;
    term_y = MATCHING_WIN_Y - ABS(p2->y - p1->y);
    term_y += (p1->y + p2->y) >> 1;
```

```
            term_x = win_x - ABS(p2->x - p1->x);
            term_x = (term_x + win_x) << 4;
            return (term_x*term_y) >> 8;
    }
    static int32_t self_match(aura_circbuf_t * ctx, int32_t offset, int32_t win_x)
    {
        int32_t cur_idx;    // idx of 'real' pt without offset
        int32_t match_idx;  // idx of 'matching' pt with offset
        int32_t score = 0;
        int32_t buf_len_minus_one = ctx->buf_len - 1;
        aura_xy_t * cur_pt;
        aura_xy_t match_pt;
        // init idxs
        match_idx = ctx->first_idx;
        cur_idx = match_idx;
        // For each point find the matching one
        while (cur_idx != ctx->last_idx) {
            cur_pt = &(ctx->buf[cur_idx]);
            if (cur_pt->y <= MATCHING_MIN_Y) {
                cur_idx = (cur_idx == buf_len_minus_one) ? 0 : cur_idx + 1;
    //aura_circbuf_inc(ctx, cur_idx);
                continue;
            }
            while (match_idx != ctx->last_idx) {
                match_pt = ctx->buf[match_idx];
                match_pt.x += offset;
                if (match_pt.x > cur_pt->x + win_x) {
                    // Too far away!
                    break;
                }
                if (match_pt.y <= MATCHING_MIN_Y || ABS(match_pt.y -
    cur_pt->y) > MATCHING_WIN_Y) {
                    // Not an interesting point
                    match_idx = (match_idx == buf_len_minus_one) ? 0 :
    match_idx + 1; //aura_circbuf_inc(ctx, match_idx);
                    continue;
                }
                if (match_pt.x > cur_pt->x - win_x) {
                    // We got a match ! (Tinder(c))
                    score += matching_score(cur_pt, &match_pt, win_x);
                }
                match_idx = (match_idx == buf_len_minus_one) ? 0 :
    match_idx + 1; // aura_circbuf_inc(ctx, match_idx);
            }
            cur_idx = (cur_idx == buf_len_minus_one) ? 0 : cur_idx + 1;
    //aura_circbuf_inc(ctx, cur_idx);
            // Put the matching idx slightly back in time
            match_idx = (match_idx == 0) ? buf_len_minus_one : match_idx - 1;
    //aura_circbuf_dec(ctc_match_idx);
            match_idx = (match_idx == 0) ? buf_len_minus_one : match_idx - 1;
    //aura_circbuf_dec(ctx, match_idx);
        }
        return score;
    }
```

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

I claim:

1. A method implemented in a system that comprises an apparatus including a processing circuitry, a memory circuit, and one or more transceivers, the method comprising:
  positioning a sensing pad that includes a sensor under a mattress;
  receiving, by said one or more transceivers, a biosignal of a patient positioned on said mattress, the biosignal being detected by the sensor;
  processing, by said processing circuit, the detected biosignal to identify a plurality of extrema points in the detected biosignal;
  comparing, by said processing circuit, the identified extrema points with a plurality of sets of reference points stored in the memory circuitry, wherein each set of reference points is obtained by shifting the identified extrema points by a respective offset in time, each respective offset in time corresponding to a respective frequency of the biosignal;
  identifying, by said processing circuit, the set of reference points that most closely fit the identified extrema points,
  determining, by said processing circuit, a frequency of the biosignal using the frequency corresponding to the identified set of reference points;
  transmitting, by said one or more transceivers, a signal indicative of the determined frequency of the biosignal to an output device of the system, and
  notifying, by said output device, the patient of a health information associated with the determined frequency of the biosignal, wherein the biosignal comprises information indicative of at least one of: heart rate, respiration rate.

2. The method as claimed in claim 1, wherein the biosignal comprises at least one of: ballistocardiogram signal, impedance plethysmogram signal.

3. The method as claimed in claim 1, wherein identifying the set of reference points that most closely fit the identified extrema points comprises assigning a value to points within the sets of reference points where the value provides an indication of distance between the reference points and the identified extrema points.

4. The method as claimed in claim 3, wherein identifying the set of reference points that most closely fit the identified extrema points comprises identifying the set of reference points with the highest assigned values.

5. The method of claim 3 wherein each reference point is assigned a score, where the score is indicative of how close the reference point is to the closest identified extrema.

6. The method of claim 3 wherein a total score for a set of reference points is determined by summing the values assigned to each of the reference points.

7. The method as claimed in in claim 3, wherein identifying the set of reference points comprises using a matching window.

8. The method as claimed in claim 7, comprising determining the distance between an identified extrema point and a reference point along one or more axis of the matching window to determine how closely a reference point fits an identified extrema point.

9. The method of claim 7, wherein the duration of the detected biosignal is at least double the period of the frequency represented by the set of reference points.

10. The method as claimed in claim 1, wherein the sets of reference points are obtained from the detected biosignal.

11. The method as claimed in claim 1, comprising filtering the detected biosignal.

12. The method of claim 1, wherein the set of reference points are obtained by applying an offset to the identified extrema points to represent different frequencies.

13. The method of claim 12, wherein the offsets of the plurality of reference points cover an expected range of the frequency of the biosignal, the expected range being a heart rate between 35 to 110 beats per minute.

14. The method of claim 12, further comprising: generating the plurality of sets of reference points and storing them.

15. The method of claim 1, wherein, once the extrema of the biosignal are obtained, the remainder of the signal is not used.

16. The method as claimed in claim 1, wherein the notifying includes displaying on a display of the output device the health information in form of a graph or a number, or both, indicative of the determined frequency.

17. The method as claimed in claim 1, wherein the notifying includes one or more of:
    displaying on a display of the output device the health information in form of a graph or a number, or both, indicative of the determined frequency,
    emitting an audio signal, and
    providing a vibration to the patient with a vibrator.

18. The method as claimed in claim 1, wherein the health information is heart rate and the method further comprises emitting an alarm by said output device when the heart rate of the patient is below a predetermined frequency.

19. An apparatus comprising a processing circuitry, a memory circuitry, and one or more transceivers, wherein the processing circuitry is configured for:

processing a biosignal of a patient detected by a sensor to identify a plurality of extrema points in the detected biosignal, the biosignal being detected by said sensor arranged in a sensing pad positioned under a mattress and said biosignal being associated with the patient that is positioned on said mattress;

comparing the identified extrema points with a plurality of sets of reference points stored in the memory circuitry wherein each set of reference points is obtained by shifting the identified extrema points by a respective offset in time, each respective offset in time corresponding to a respective frequency of the biosignal;

identifying the set of reference points that most closely fit the identified extrema points; and determining a frequency of the biosignal using the frequency corresponding to the identified set of reference points, and wherein the one or more transceivers are configured for receiving the detected biosignal detected by the sensor, transmitting a signal indicative of the determined frequency of the biosignal to an output device that notifies the patient of a health information associated with the determined frequency of the biosignal, and wherein the biosignal comprises information indicative of at least one of: heart rate, respiration rate.

20. A system comprising:
a sensing pad including one or more sensors, wherein the one or more sensors are configured for acquiring a detected biosignal of a patient when the sensing pad is positioned under a mattress and the patient is positioned on said mattress;
an output device, and
an apparatus including a processing circuitry, a memory circuitry, and one or more transceivers,
wherein the processing circuitry is configured for:
    processing the detected biosignal to identify a plurality of extrema points in the detected biosignal;
    comparing the identified extrema points with a plurality of sets of reference points stored in the memory circuitry wherein each set of reference points is obtained by shifting the identified extrema points by a respective offset in time, each respective offset in time corresponding to a respective frequency of the biosignal;
    identifying the set of reference points that most closely fit the identified extrema points; and
    determining a frequency of the biosignal using the frequency corresponding to the identified set of reference points, and
    wherein the one or more transceivers are configured for receiving the detected biosignal detected by the one or more sensors, and
        transmitting a signal indicative of the determined frequency of the biosignal to said output device, and
    wherein said output device is configured for notifying the patient of a health information associated with the determined frequency of the biosignal, and
    wherein the biosignal comprises information indicative of at least one of: heart rate, respiration rate.

21. A system according to claim 20, wherein the system is a single device.

22. A non-transitory computer readable medium comprising computer program instructions that, when executed by an apparatus that comprises a processing circuitry, a memory circuit and one or more transceivers, enable:

receiving, by said one or more transceivers, a biosignal detected by a sensor arranged in a sensing pad that is positioned under a mattress, said biosignal being associated with a patient that is positioned on said mattress;

processing, by said processing circuit, the detected biosignal to identify a plurality of extrema points in ft the detected biosignal;

comparing, by said processing circuit, the identified extrema points with a plurality of sets of reference points stored in a memory circuitry, wherein each set of reference points is obtained by shifting the identified extrema points by a respective offset in time, each respective offset in time corresponding to a respective frequency of the biosignal;

identifying, by said processing circuit, the set of reference points that most closely fit the identified extrema points;

determining, by said processing circuit, a frequency of the biosignal using the frequency corresponding to the identified set of reference points, and transmitting, by said one or more transceivers, a signal indicative of the determined frequency of the biosignal to an output device that notifies the patient of a health information associated with the determined frequency of the biosignal, wherein the biosignal comprises information indicative of at least one of: heart rate, respiration rate.

23. A method implemented in a system comprising at least a sensor arranged in a sensing pad, an output device and an apparatus including a processing circuitry, a memory circuit and one or more transceivers, the apparatus being coupled to the sensor and the output device, the method comprising:

positioning the sensing pad that includes the sensor under a mattress;

acquiring, by the sensor, a detected biosignal of a patient positioned on said mattress;

receiving, by the one or more transceivers, the acquired biosignal;

processing, by the processing circuitry, the detected biosignal to determine a plurality of extrema points in the detected biosignal;

comparing, by the processing circuitry, the determined extrema points with a plurality of sets of reference points stored in the memory circuitry, wherein each set of reference points is obtained by shifting the identified extrema points by a respective offset in time, each respective offset in time corresponding to a respective of the biosignal;

identifying, by the processing circuitry, the set of reference points that most closely fit the determined extrema points;

determining, by the processing circuitry, a frequency of the biosignal using the frequency corresponding to the identified set of reference points;

transmitting, by said one or more transceivers, a signal indicative of the determined frequency of the biosignal to an output device, and notifying, by said output device, the patient of a health information associated with the determined frequency of the biosignal, wherein the biosignal comprises information indicative of at least one of: heart rate, respiration rate.

* * * * *